United States Patent

Wu

[11] Patent Number: 5,550,305
[45] Date of Patent: Aug. 27, 1996

[54] ETHYLENE TRIMERIZATION

[75] Inventor: Feng-Jung Wu, Baton Rouge, La.

[73] Assignee: Amoco Corporation, Chicago, Ill.

[21] Appl. No.: 227,433

[22] Filed: Apr. 14, 1994

Related U.S. Application Data

[63] Continuation-in-part of Ser. No. 25,524, Mar. 3, 1993, abandoned, which is a continuation-in-part of Ser. No. 914,489, Jul. 14, 1992, which is a continuation of Ser. No. 777,137, Oct. 16, 1991, abandoned.

[51] Int. Cl.$^6$ ................................................ C07C 2/36
[52] U.S. Cl. ........................ 585/513; 585/511; 585/512; 585/514; 585/520
[58] Field of Search ............................... 585/511, 512, 585/513, 514, 520, 521, 527

[56] References Cited

U.S. PATENT DOCUMENTS

| | | | |
|---|---|---|---|
| 3,231,550 | 1/1966 | Manyik et al. | 260/88.2 |
| 3,242,099 | 3/1966 | Manyik et al. | 252/249 |
| 3,300,458 | 1/1967 | Manyik et al. | 260/88.2 |
| 3,347,840 | 10/1967 | Manyik et al. | 260/94.9 |
| 3,695,853 | 10/1972 | Klanberg | 423/299 |
| 4,668,838 | 5/1987 | Briggs | 585/513 |
| 4,777,315 | 10/1988 | Levine et al. | 585/512 |

OTHER PUBLICATIONS

Rottinger et al: Journal of Organometallic Chemistry, vol. 213, 1981, pp. 1–9.
Hermes et al: Inorganic Chemistry, vol. 29, 1990, pp. 313–317.
Thomas et al: Journal of American Chemical Society, vol. 113, 1982, pp. 893–902.
Manyik, et al., *Journal of Catalysis*, 47, 197–209 (1977).
Mews, *Angew. Chem. Int. Ed. Engl.* 16 (1977) 56.
Gray, et al., *J. Chem. Soc. Dalton Trans.* 1984.
Arif, et al., *Inorg. Chem.* 1986, 25, 1080–1084.

*Primary Examiner*—Ponnathapura Achutamurthy
*Attorney, Agent, or Firm*—Stephen L. Hensley

[57] ABSTRACT

Ethylene is trimerized to form 1-hexene by using a catalyst comprising an aluminoxane and polydentate phosphine, arsine, and/or stibine coordination complex of a chromium salt.

9 Claims, No Drawings

ETHYLENE TRIMERIZATION

This application is a continuation-in-part of application Ser. No. 08/025,524, filed Mar. 3, 1993, now abandoned which is a continuation-in-part of application Ser. No. 07/914,489, filed Jul. 14, 1992 which is a continuation of application Ser. No. 07/777,137, filed Oct. 16, 1991, now abandoned.

This invention relates generally to the oligomerization of ethylene and more specifically to the preparation of 1-hexene by the trimerization of ethylene using a catalyst which includes an aluminoxane and a chromium complex containing a coordinating polydentate phosphine, stibine or arsine ligand, such as a tridentate phosphine complex of a chromium salt.

My copending application Ser. No. 07/914,489, whose teachings are incorporated herein by reference, discloses an ethylene oligomerization/trimerization process which uses a catalyst comprising a chromium complex which contains a coordinating polydentate ligand and an aluminoxane to produce high quality α-olefins which are enriched in 1-hexene. Suitable ligands include cyclic polyamines, and polypyrazolyl borates.

In accordance with this and my copending application Ser. No. 08/025,524, now abandoned, whose teachings are incorporated herein by reference, I have now found that certain polydentate ligand complexes of chromium salts in combination with aluminoxanes can catalyze ethylene oligomerization, and especially ethylene trimerization to form 1-hexene, with a very high degree of selectivity, e.g. about 96%.

Prior art ethylene trimerization processes, such as are described in U.S. Pat. Nos. 4,668,838 and 4,777,315 which use mixtures of a chromium compound, an aluminoxane and a third component selected from hydrocarbyl isonitriles, amines and ethers, are reported to produce amounts of polyethylene ranging from about 18 to 90+ percent as a coproduct. Such polyethylene not only decreases the yield of desirable product but also causes problems due to polymer build-up which would be expected to hamper the commercial use of such processes. In contrast, the process and catalyst of the invention can readily avoid the coproduction of significant amounts of polyethylene (less than about 2.0 wt. % and normally from 0 to 1.5 wt. %) with most of the byproducts being short chain olefins, particularly, 1-butene.

The catalysts of the invention also retain >90 percent of the initial activity after 12 hours of reaction time, giving a catalyst productivity of, for example, about 8,000 g or more of hexene/g Cr compound, whereas the productivity of the catalysts of the above mentioned prior art processes are limited by polyethylene formation to the range of about 500 to 1,000 g hexene/g chromium compound. The catalysts of the invention are also more thermally stable than the catalysts of Applicant's application Ser. No. 07/914,489 thereby giving a similar improvement in catalyst life.

In accordance with this invention there is provided a process for the trimerization of ethylene which process comprises reacting ethylene using a catalyst comprising an aluminoxane and a polydentate phosphine, arsine and/or stibine coordination complex of a chromium salt so as to form 1-hexene.

Also provided is an ethylene trimerization catalyst composition comprising an aluminoxane and a polydentate phosphine, arsine and/or stibine coordination complex of a chromium salt.

Aluminoxanes for use in the process of the invention can be prepared as known in the art by reacting water or water containing materials with trialkylaluminum compounds in proportions of from about 0.5 to 1.2 equivalents of water and, preferably, 0.8 to 1.0 equivalents of water per equivalent of trialkylaluminum. For example, Manyik et al U.S. Pat. No. 3,300,458 prepare alkylaluminoxane by passing a hydrocarbon solvent through water to form a wet hydrocarbon solvent and mixing the wet hydrocarbon solvent with an alkyl aluminum/hydrocarbon solvent mixture in a conduit.

Schoenthal et al. U.S. Pat. No. 4,730,071 show the preparation of methylaluminoxane by dispersing water in toluene using an ultrasonic bath and then adding a toluene solution of trimethyl aluminum to the dispersion. Schoenthal et al U.S. Pat. No. 4,730,072 is similar except it uses a high speed, high shear-inducing impeller to form the water dispersion.

Edward et at. U.S. Pat. No. 4,772,736 describe an aluminoxane process in which water is introduced below the surface of a solution of hydrocarbyl aluminum adjacent to a stirrer which serves to immediately disperse the water in the hydrocarbon solution.

The preparation of alkyl aluminoxanes from $R_2AlOLi$ formed by reacting $AlR_3$ and anhydrous lithium hydroxide, and $R_2AlCl$ has been reported in the literature, for example, Ueyama et al., Inorganic Chemistry, 12, No. 10, 2218 (1973) and Aoyazi et al., Inorganic chemistry, 12, No. 11, 2702 (1973).

Sinn et at. U.S. Pat. No. 4,404,344 prepare methylaluminoxane by adding trimethyl aluminum to a slurry of $CuSO_4 \bullet 5H_2O$ in toluene. Introducing water as a metal hydrate controls its reactivity with the trimethyl aluminum. Kaminsky et at. U.S. Pat. No. 4,544,762 is similar except it uses an aluminum sulfate salt hydrate to supply the water. Likewise, Welborn et al. U.S. Pat. No. 4,665,208 describe the use of other metal salt hydrates such as $FeSO_4 \bullet 7H_2O$ as a water source in preparing aluminoxane.

Hydrocarbylaluminoxanes may exist in the form of linear or cyclic polymers with the simplest compounds being a tetraalkylaluminoxane such as tetraethylaluminoxane, $(C_2H_5)_2AlOAl(C_2H_5)_2$. Preferred aluminoxanes are prepared from trialkyl aluminum compounds such as triethyl aluminum, tri-n-butyl aluminum, triisobutyl aluminum, tri-n-hexyl aluminum, tri-octyl aluminum and the like. Of these, the more preferred are the compounds having $C_6$ or higher alkyl groups which have better solubility in the hydrocarbon solvent reaction medium. The aluminoxanes used to form the catalyst are preferably contained in organic solvents in concentrations of from about 0.3 to 30 weight percent of total solvent plus aluminoxane.

A trialkylaluminum compound can also be included in the catalyst (0.1 to 1.0 mole per mole of aluminoxane).

The chromium complexes which, upon mixing with an aluminoxane, catalyze ethylene oligomerization and especially trimerization in accordance with the process of the invention can be represented by the formula: $LCrX_n$, wherein L is a coordinating polydentate phosphine, arsine and/or stibine ligand and X represents anions which can be the same or different and n is an integer of 2 to 4. Such complexes can be in the form of oligomers, i.e. $(LCrX_n)_y$ where y is 2 to 8. By "polydentate" is meant that the ligand contains multiple donor atoms for coordination with chromium.

Preferred polydentate ligands include the following types:

(a) $RY(R'ZR''R''')_2$ wherein R, R" and R''' are hydrogen or $C_1$ to about $C_{20}$ hydrocarbyl and where R" and R''' can join to form a five membered ring which includes Z; R' is $C_1$ to about $C_{10}$ hydrocarbyl; and Y and Z are individually phosphorus, arsenic or antimony;

(b) $CH_3E(R'ZR''_2)_3$ wherein E is C, Si, Ge or Sn and R', R" and Z are as defined in (a) above;

(c) $E'(R'ZR''_2)_3$ wherein E' is nitrogen, phosphorus, arsenic or antimony and R', R" and Z are as defined in (a) above; and (d) A—ZR—B wherein A is an integer of 9 to 18, B is an integer of 3 to 6, R is a $C_1$ to $C_{10}$ alkyl group such as a methyl, ethyl, propyl, butyl, pentyl, hexyl or higher alkyl group or a $C_6$ to $C_{20}$ aromatic group such as benzyl and Z is phosphorous, arsenic or antimony. The abbreviations, such as 9-PR-3, 10-PR-3, 12-PR-4 and the like, used for the phosphine ligands correspond to those used for crown ethers because they are their phosphorus analogues. For example, 9-PR-3 denotes a nine membered ring with 3 equally spaced phosphorus atoms. The most preferred coordinating polydentate ligands of this type are facially coordinating tridentate ligands such as 9-PMe-3.

In the ligands of types (a), (b) and (c) each (R'ZR") moiety can be different so as to provide a mixture of donors in the same complex. The ligands of types (a), (b), (c), and (d) can be modified to attach to a polyethylene chain (molecular wt.=1000 or higher) so that the resulting catalyst is homogeneous (soluble) at elevated temperature but becomes heterogeneous (insoluble) at 25° C. This technique facilitates the recovery of the catalyst from the reaction products for reuse and has been used with other catalysts as described, for example, by D. E. Bergbreiter et al. J. Chem. Soc., Chem. Commun., 337–338 (1985); J. Org. Chem. (1986) 51, 4752–4760; and J.A.C.S, (1987), 109, 177–179.

Non-limiting examples of specific tridentate phosphine ligands include:

for type (a), $EtP(C_2H_4PEt_2)_2$, whose chemical name is bis-(2-diethylphosphinoethyl)ethylphosphine;

for type (b), $CH_3C(CH_2PEt_2)_2$, whose chemical name is 1,1,1-tris(diethylphosphinomethyl)ethane;

for type (c), $P(C_2H_4PEt_2)_3$, whose chemical name is tris(2-diethylphosphinoethyl)phosphine; and for type (d), 9-PMe-3, whose chemical name is 1,4,7-trimethyl-1,4,7-triphosphinocyclononane.

Other specific examples are:

$CH_3C(CH_2PPh_2)_3$ $PhP(CH_2CH_2PPh_2)_2$ $CyP(CH_2CH_2PCy_2)_2$ $CyP(CH_2CH_2PEt_2)_2$ $n-PrP(CH_2CH_2PEt_2)_2$ $EtP(C_3H_6PEt_2)_2$ $N(C_2H_4PEt)_3$ $PhP(o-C_6H_4PEt_2)_2$ wherein Ph=phenyl, Cy=cyclohexyl, Me=methyl, Et=ethyl and Pr=propyl. The arsine and stibine analogues of these ligands could also be prepared, for example:

$PhAs(o-C_6H_4AsPh_2)_2$ $MeAs(o-C_6H_4AsMe_2)_2$ $MeSb(C_2H_4SbMe_2)_2$ $MeAs(C_3H_6AsMe_2)_2$

By a coordinating polydentate ligand is meant a ligand that sterically encumbers the chromium atom in such a way that the rate of chain propagation is decreased so that oligomerization, especially trimerization, rather than polymerization occurs. For example, ligands which occupy three adjacent coordination sites about an octahedral chromium atom.

Examples of suitable anions, X, include, but are not limited to, halides ($Cl^-$, $Br^-$, $I^-$, $F^-$), alkoxides ($OR^-$), carboxylates ($O_2CR^-$), Oxo($O^{-2}$) and the like. These anions are initially the anion portion of the chromium compounds used to make the complex. The chromium in the compounds is initially in the oxidation state of II to VI and is preferably in the oxidation state of II, III or IV.

The chromium complexes can be prepared according to procedures set forth in the literature. For example L. R. Gray et al., J. Chem. Soc. Dalton. Trans. (1984), 47–53, A. M. Arif et al. Inorg. Chem., Vol. 25, No. 8, 1986, 1080–1084, and Diel et at., J. Am. Chem. Soc. 1982, 104, 4700–4701.

The chromium complex and aluminoxane are combined in proportions to provide Al/Cr molar ratios of from about 1:1 to 10,000 to 1 and, preferably, from about 5:1 to 500 to 1. The amount of catalyst used is selected to provide the desired reaction rates at any particular reaction scale. (The presence of amounts of about 0.001 mmole or more and preferably from about 0.1 to 10 mmoles of chromium catalyst in a 300 ml reactor are effective to catalyze the reaction.) Catalyst mixing is preferably done at low temperatures of 0° to 35° C. The presence of ethylene during catalyst mixing at these temperatures resulted in no significant difference in catalyst properties when compared with catalysts prepared in the absence of ethylene. Ethylene provided a protective effect at temperatures above 55° C.

The reaction with ethylene is carried out in an inert solvent. Any inert solvent which does not react with aluminoxane can be used. The preferred solvents are aliphatic and aromatic hydrocarbons and halogenated hydrocarbons such as, for example, toluene, xylene, ethylbenzene, cumene, mesitylene, heptane, cyclohexane, methylcyclohexane, 1-hexene, 1-octene, chlorobenzene, dichlorobenzene, and the like. The amount of solvent is not particularly critical and generally ranges from about 50 to 99 wt. percent of the initial reaction mixture.

Reaction temperatures and pressures are chosen to optimize reaction rates and selectivity. In general temperatures of from about 35° to 200° C. are used and preferably 80° to 120° C. Ethylene pressures can range from atmospheric to 3000 psig and preferably from about 100 to 1500 psig. Temperature and pressure affect reaction rate and purity in the following way: both higher temperature and higher ethylene pressure increase reaction rate; higher ethylene pressures give better purity by forming less internal olefins, whereas higher temperatures increase the formation of internal olefins.

The invention is further illustrated by, but is not intended to be limited to, the following examples.

EXAMPLE 1

Preparation of Triphosphine Chromium Trichloride

Preparation of $n-PrP(CH=CH_2)_2$

To a 1.0M solution of vinylMgBr (70 mmol) in THF at 0° C. was added a solution of $n-PrPCl_2$ (3.75 g, 25.9 mmol) in 35 ml THF over 1 hour. The solution was allowed to warm slowly and stirred overnight. To the resulting suspension was added degassed saturated $NH_4Cl$ solution (50 ml) slowly to kill the unreacted vinylMgBr. The organic phase was separated from the aqueous phase using a cannula. The remaining aqueous phase was washed with two 40-ml portions of $Et_2O$, which were then combined with the organic phase, dried over sodium carbonate and distilled at ambient pressure under inert atmosphere to give 2.0 g (60% yield) of n-PrP($C_2H_3$)$_2$ (b.p.=143° C.).

Preparation of n-PrP($C_2H_4PEt_2$)$_2$

A mixture of n-PrP(CH=$CH_2$)$_2$ (1.29 g, 10.0 mmol), $Et_2$PH (2.25 g, 25.0 mmol) and 2,2'-azobis(isobutyronitrile) (AIBN, 30 mg) in a closed flask under inert atmosphere was irradiated by a GE Sunlamp (275 W) one foot away for 24 hours. The resulting colorless liquid was stripped of volatiles under vacuum and vacuum distilled to give 3.1 g (97% yield) of product collected at 132°–135° C./0.35 mmHg. $^{31}$P-NMR (toluene): δ–18.5 (2P); δ–22.8 (1P).

Preparation of [n-PrP($C_2H_4PEt_2$)$_2$]$CrCl_3$

A mixture of n-PrP($C_2H_4PEt_2$)$_2$ (2.30 g, 7.46 mmol) and anhydrous $CrCl_3$ (0.40 g, 2.50 mmol) in a closed flask under vacuum was heated with stirring at 135° C. for 1 hour. The reaction mixture at this stage contained four compounds: excess ligand (heptane-soluble), purple $LCrCl_3$ (toluene-soluble), blue $LCrCl_3$ ($CH_2Cl_2$-soluble), and unreacted $CrCl_3$. Separation was achieved by solubility difference. The resulting blue cake was extracted with 20 ml of toluene, filtered, and washed with toluene until colorless. Toluene was removed from the combined purple filtrate, the residue was extracted with heptane, filtered to give a purple solid and unreacted ligand in heptane. The insoluble materials were a mixture of a blue solid and unreacted $CrCl_3$. Separation was achieved by extraction with $CH_2Cl_2$. Unreacted $CrCl_3$ (0.05 g) was recovered. Results: blue solid; 0.65 g, purple solid; 0.35 g. The combined yield was quantitative based on reacted $CrCl_3$. The blue and purple solids are both active in the ethylene trimerization reaction. Anal. for the blue compound, Calcd: P, 19.91; Cl, 22.79; Cr, 11.14; C, 38.60; H, 7.56. Found P, 19.77; Cl, 23.14; Cr, 11.46; C, 38.20; H 7.65.

The following diagram shows the X-ray crystal structure of the purple product:

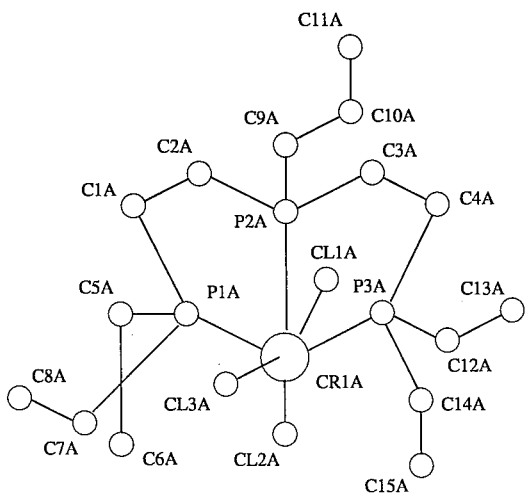

Another ligand-chromium complex, [CyP($C_2H_4PEt_2$)$_2$]$CrCl_3$, where Cy is cyclohexyl, was prepared analogously.

EXAMPLE 2

Ethylene Trimerization Reaction

The reaction was carried out in a 300 ml Parr stainless-steel reactor to which a liquid addition bomb was connected for the purpose of adding the aluminoxane solution under ethylene pressure. To the reactor containing a solution of [n-PrP($C_2H_4PEt_2$)$_2$]$CrCl_3$ (45 mg, 0.096 mmol) and pentadecane (0.267 g, as internal reference for gas chromatography) in 90 ml of toluene at 25° C. under 250 psig of ethylene pressure was added a solution of n-hexylaluminoxane (5.0 mmol) in 10 ml of toluene using ethylene gas which brought the pressure to 300 psig. The chain-growth reaction was then carried out with continuous ethylene feed at 95° C./610 psig for one hour (stirring rate: 800 RPM), during which time 22 g of ethylene was consumed. The reaction was terminated by pressing methanol into the reactor to deactivate the catalyst. The reactor was cooled to 10° C., vented, and a sample was withdrawn for GC analysis which showed the following results: $C_4$: 4.3%, $C_6$: 94.3%, $C_8$: 0.2%, $C_{10}$: 0.9%. The polymer produced was only 0.1% and the purity of 1-hexene was 92.6% with major impurities being internal hexenes. The weights of the carbon fractions were calculated using measured response factors and mimic experiments to simulate the operational loss of light olefins.

Results of this and other Examples 3–11 with varied reaction conditions are summarized in Table I. Except for Example 11, only small amounts of polyethylene were formed in the process and the butene co-product ranged from about 3 to 15 percent. Hexene production was at least 80%, Impurities in the complex can cause increased polymer formation, as per Example 11, such that if such polymer formation occurs, the purity of the complex should be checked. The process by avoiding significant amounts of polyethylene has the advantages that the reactions in a commercial operation would not require frequent cleaning as would be the case with the prior art processes and also the catalyst life is extended. For example a catalyst of n-PrP($C_2H_4PEt_2$)$_2$ $CrCl_3$ retains>90% of its initial activity even after 12 hours of reaction, giving a catalyst productivity of about 8000 g hexene/g Cr catalyst compound. The catalysts according to the prior art gave catalyst productivities in the range of only 500–1,000.

TABLE I

| | | | | | | | | | | | |
|---|---|---|---|---|---|---|---|---|---|---|---|
| Catalyzed Ethylene Trimerization Reactions[1] | | | | | | | | | | | |
| Example | Catalyst (mmol)[2] | | Pressure | Temperature | | Distribution (wt. %) | | | | Purity wt. % | Polymer |
| No. | Cr | Al | (psig) | (°C.) | Activity[3] | $C_4$ | $C_6$ | $C_8$ | $C_{10}$ | 1-hexene | (wt. %) |
| 3 | .096 | 5.0 | 610 | 95 | 8,200 | 4.1 | 94.3 | .17 | .64 | 92.6 | 0.6 |
| 4 | .100 | 5.0 | 620 | 80 | 3,200 | 3.1 | 94.4 | .23 | .52 | 94.4 | 1.5 |
| 5 | .096 | 5.0 | 700 | 115 | 11,100 | 9.6 | 89.3 | .20 | .65 | 87.4 | 0 |

TABLE I-continued

| Example No. | Catalyst (mmol)[2] Cr | Al | Pressure (psig) | Temperature (°C.) | Activity[3] | Distribution (wt. %) $C_4$ | $C_6$ | $C_8$ | $C_{10}$ | Purity wt. % 1-hexene | Polymer (wt. %) |
|---|---|---|---|---|---|---|---|---|---|---|---|
| 6 | .088 | 5.0 | 970 | 94 | 17,000 | 3.2 | 94.9 | .11 | .59 | 93.7 | 1.1 |
| 7 | .084 | 5.0 | 960 | 85 | 11,700 | 2.3 | 96.4 | 0.1 | 0.6 | 95.0 | 0.4 |
| 8 | .069 | 5.0 | 610 | 106 | 7,800 | 8.6 | 90.3 | .23 | .62 | 90.0 | 0.1 |
| (purple [n-PrP($C_2H_4PEt_2$)$_2$]CrCl$_3$ | | | | | | | | | | | |
| 9 | .084 | 6.0 | 610 | 94 | 5,700 | 15.0 | 83.0 | .13 | .42 | 91.9 | 1.3 |
| (propylaluminoxane was used) | | | | | | | | | | | |
| 10 | .097 | 10.0 | 630 | 95 | 14,000 | 10.5 | 88.7 | .38 | .26 | 90.2 | 0.1 |
| (blue [CyP($C_2H_4PEt_2$)$_2$]CrCl$_3$ and butylaluminoxane were used) | | | | | | | | | | | |
| 11[4] | .071 | 5.0 | 590 | 94 | 7,900 | 4.5 | 82.0 | 0.8 | 0.5 | 93.2 | 12.0 |

[1]Reactions were carried out in 100 ml toluene for one hour.
[2]Hexylaluminoxane and blue [n-PrP($C_2H_4PEt_2$)$_2$]CrCl$_3$ were used unless otherwise noted.
[3]Activity = mol ethylene/mol Cr/h.
[4]A less pure complex was used, prepared from CrCl$_3$THF$_3$, which resulted in a high amount of polymer coproduct.

Comparison 1

The triphosphine ligand, n-PrP($C_2H_4PEt_2$)$_2$ was used as part of a three component CrX$_3$/aluminoxane/ligand system, where X is 2-ethylhexanoate (a mixed system as suggested in Briggs U.S. Pat. No. 4,668,838 as opposed to a preformed chromium complex as per the process of the invention) A low yield of impure 1-hexene was formed along with a similar amount of undesirable polyethylene. The main product was butenes (72%). According to the process a mixture of n-PrP($C_2H_4PEt_2$)$_2$ (62 mg, 0.2 mmol) in toluene and Cr(2-ethylhexanoate)$_3$ in heptane (10% solution, 0.48 g solution, 0.1 mmol Cr) was allowed to react for 10 minutes with stirring in a dry box. To it was added isobutylaluminoxane (6.0 mmol) in toluene. The total amount of toluene was about 100 ml and 115 mg of pentadecane was added as an internal reference for gas chromatography. The above mixture was transferred to a 300 ml Parr reactor, sealed, and pressured with 25 g. of ethylene (33° C./415 psig). The reaction was heated to 92°–105° C. and ethylene pressure dropped from 680 psig to 390 psig over 8 minutes. After cooling, unreacted ethylene was vented at 31° C. (230 psig). The product contained 1.2 grams of polymer (12%), 1.5 grams of hexenes (15%, purity 90.9%) and 7.0 grams of butenes (72%, purity 88.6% and a trace of $C_8$ and higher materials). The results show that using a tridentate ligand as a third component, as opposed to a preformed complex with chromium, not only caused a loss of trimerization activity but 12% polymer formation occurred. Also, a lower vinyl purity resulted. Note that this reaction used excess (2:1) ligand. Even more polymer would be expected to form if less ligand is used, based on the results obtained when using the previous 9-NMe-3 ligand.

Comparison 2

A mixture of n-PrP($C_2H_4PEt_2$)$_2$ (62 mg, 0.2 mmol), anhydrous CrCl$_3$ (23 mg, 0.15 mmol) isobutylaluminoxane (5.3 g solution, 6.0 mmol), pentadecane (68 mg) in about 100 ml of toluene was stirred at room temperature in a dry box for 10 minutes. No dissolution of CrCl$_3$ was observed. The mixture was poured into a Parr (300 ml) reactor, sealed, pressurized with 25 g of ethylene and heated to 96° C. The pressure was 725 psig. Because no pressure drop was observed after 17 minutes under these conditions, the temperature was brought to 125° C. As soon as the temperature reached 120° C. (800 psig) ethylene consumption took place. Within 5 minutes the pressure dropped from 800 to 160 psig at 120°–128° C. The reactor was cooled without quenching the catalyst and unreacted ethylene was released at 30° C. The solution was light purple with about ⅔ of the CrCl$_3$ remaining unreacted. The product by GC contained 90% butenes (76.4% pure), 9% hexene (74.2% pure) and a trace of polymer. The results show that a poor yield of impure $C_6$ was produced and, although only a trace of polymer was found, the major product was butenes.

What is claimed is:

1. A process for the trimerization of ethylene, said process comprising reacting ethylene, at a temperature of from about 35° to 200° C. and an ethylene pressure of from about atmospheric to 3000 psig, using a catalyst comprising an aluminoxane and at least about 0.001 mmole of a polydentate phosphine, arsine and/or stibine coordination complex of a chromium salt, wherein:

a) the mole ratio of aluminum to chromium in the catalyst is from about 1:1 to about 10,000:1;
   b) said complex has the formula LCrX$_n$, wherein X represents anions which can be the same or different, n is an integer of 2 to 4 and L is a coordinating polydentate phosphine, arsine and/or stibine ligand selected from the group consisting of:
   1) ligands of the formula:

   RY(R'ZR"R''')$_2$ wherein R, R" and R''' are hydrogen or $C_1$ to about $C_{20}$ hydrocarbyl and where R" and R''' can join to form a five membered ring which includes Z; R' is $C_1$ to about $C_{10}$ hydrocarbyl; and Y and Z are individually phosphorus, arsenic or antimony;
   2) ligands of the formula:

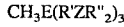
   CH$_3$E(R'ZR"$_2$)$_3$ wherein E is C, Si, Ge or Sn; R$^1$ is $C_1$ to about $C_{20}$ hydrocarbyl; each R" is individually hydrogen or $C_1$ to about $C_{10}$ to hydrocarbyl and each Z is individually phosphorus, arsenic or antimony;
   3) ligands of the formula:

   E'(R'ZR"$_2$)$_3$ wherein E' is nitrogen, phosphorus, arsenic or antimony; R' is $C_1$ to about $C_{20}$ hydrocarbyl; each R" is individually hydrogen or $C_1$ to about $C_{10}$ hydrocarbyl and each Z is individually phosphorus, arsenic or antimony; and 4) ligands of the formula:

A—ZR—B wherein A represents the number of atoms in the ring and is an integer of 9 to 18, B represents the number of Z atoms in the ring and is an integer of 3 to 6, R is a $C_1$ to $C_{10}$ alkyl or a $C_6$ to $C_{20}$ aryl group and Z is phosphorus, arsenic or antimony; so as to form 1-hexene.

2. The process according to claim 1 wherein said complex is in the form of an oligomer, $(LCrX_n)_y$ where y is 2 to 8.

3. The process according to claim 1 wherein said polydentate ligand has the formula:

RY(R'ZR"R''')$_2$ wherein R, R" and R''' are hydrogen or $C_1$ to about $C_{20}$ hydrocarbyl and where R" and R''' can join to form a five membered ring which includes Z; R' is $C_1$ to about $C_{10}$ hydrocarbyl; and Y and Z are individually phosphorus, arsenic or antimony.

4. The process according to claim 1 wherein said polydentate ligand has the formula:

CH$_3$E(R'ZR"$_2$)$_3$ wherein E is C, Si, Ge or Sn; $R^1$ is $C_1$ to about $C_{20}$ hydrocarbyl; each R" is individually hydrogen or $C_1$ to about $C_{10}$ hydrocarbyl and each Z is individually phosphorus, arsenic or antimony.

5. The process according to claim 1 wherein said polydentate ligand has the formula:

E'(R'ZR"$_2$)$_3$ wherein E' is nitrogen, phosphorus, arsenic or antimony; R' is $C_1$ to about $C_{20}$ hydrocarbyl; each R" is individually hydrogen or $C_1$ to about $C_{10}$ hydrocarbyl and each Z is individually phosphorus, arsenic or antimony.

6. A process according to claim 1 wherein said polydentate ligand is a ring compound and has the formula:

A—ZR—B wherein A represents the number of atoms in the ring and is an integer of 9 to 18, B represents the number of Z atoms in the ring and is an integer of 3 to 6, R is a $C_1$ to $C_{10}$ alkyl or a $C_6$ to $C_{20}$ aryl group and Z is phosphorus, arsenic or antimony.

7. The process according to claim 1 wherein L is selected from CyP(CH$_2$CH$_2$PEt$_2$)$_2$, EtP(CH$_2$CH$_2$PEt$_2$)$_2$ and n-PrP(CH$_2$CH$_2$PEt$_2$)$_2$.

8. The process of claim 1 wherein the reaction is conducted at a temperature of from about 80° to 120° C. and an ethylene pressure of from about 100 to 1500 psig, and the mole ratio of aluminum to chromium in the catalyst is from about 5:1 to 500:1.

9. The process according to claim 1 wherein less than about 2.0 wt. % polyethylene byproduct is formed.

* * * * *